United States Patent
Kenrick et al.

(10) Patent No.: US 10,370,649 B2
(45) Date of Patent: Aug. 6, 2019

(54) DEVICE AND METHOD FOR CELL NUCLEI PREPARATION

(71) Applicant: GE Healthcare UK Limited, Buckinghamshire (GB)

(72) Inventors: Michael Kenneth Kenrick, Cardiff (GB); Geraint Seymour, Cardiff (GB)

(73) Assignee: GE Healthcare UK Limited, Little Chalfont (GB)

(*) Notice: Subject to any disclaimer, the term of this patent is extended or adjusted under 35 U.S.C. 154(b) by 0 days.

(21) Appl. No.: 15/317,039

(22) PCT Filed: Jun. 17, 2015

(86) PCT No.: PCT/EP2015/063574
§ 371 (c)(1),
(2) Date: Dec. 7, 2016

(87) PCT Pub. No.: WO2016/000960
PCT Pub. Date: Jan. 7, 2016

(65) Prior Publication Data
US 2017/0121703 A1     May 4, 2017

(30) Foreign Application Priority Data
Jun. 30, 2014 (GB) .................................. 1411615.6

(51) Int. Cl.
*C12N 15/10* (2006.01)
*B01L 3/00* (2006.01)

(52) U.S. Cl.
CPC .......... *C12N 15/1006* (2013.01); *B01L 3/502* (2013.01); *C12N 15/1017* (2013.01);
(Continued)

(58) Field of Classification Search
CPC . C12N 15/1006; C12N 15/1017; B01L 3/502; B01L 2200/0631; B01L 2200/16;
(Continued)

(56) References Cited

U.S. PATENT DOCUMENTS 5,429,803 A * 7/1995 Guirguis ............... A61B 10/007
422/419
5,447,864 A    9/1995 Raybuck et al.
(Continued)

FOREIGN PATENT DOCUMENTS

EP          0297441 A2    1/1989
WO      2012/085006 A1    6/2012
(Continued)

OTHER PUBLICATIONS

International Search Report and Written Opinion regarding International Application No. PCT/EP2015/063574, dated Sep. 16, 2015, 11 pages.
(Continued)

*Primary Examiner* — Benjamin R Whatley
(74) *Attorney, Agent, or Firm* — Eversheds Sutherland (US) LLP (57) ABSTRACT

The present invention relates to the field of nucleic acid collection and storage, and in particular to the collection and long-term storage of nuclei. The invention provides a device and method which can be used to capture and store nuclei at ambient temperatures allowing the subsequent isolation of nucleic acids by passive washing with a wash buffer. The present invention also provides a kit including the device of the invention suitable for carrying out the method of the invention.

32 Claims, 7 Drawing Sheets

(52) U.S. Cl.
CPC ... *B01L 2200/0631* (2013.01); *B01L 2200/16* (2013.01); *B01L 2300/044* (2013.01); *B01L 2300/0681* (2013.01); *B01L 2300/12* (2013.01); *B01L 2400/049* (2013.01); *B01L 2400/0478* (2013.01)

(58) Field of Classification Search
CPC ....... B01L 2300/044; B01L 2300/0681; B01L 2300/12; B01L 2400/0478; B01L 2400/049
See application file for complete search history.

(56) References Cited

U.S. PATENT DOCUMENTS

| | | |
|---|---|---|
| 2007/0284300 A1 | 12/2007 | Bidlingmeyer et al. |
| 2010/0129878 A1* | 5/2010 | Parthasarathy ... B01L 3/502753 435/91.5 |
| 2012/0138544 A1 | 6/2012 | Barani |
| 2013/0137172 A1* | 5/2013 | Ririe ...................... C12M 33/00 435/306.1 |
| 2013/0284680 A1 | 10/2013 | Tortorella et al. |

FOREIGN PATENT DOCUMENTS

| | | | |
|---|---|---|---|
| WO | 2013/036819 A1 | 3/2013 | |
| WO | WO-2013036819 A1 * | 3/2013 | ......... A01K 67/0271 |
| WO | 2014/023765 A2 | 2/2014 | |
| WO | 2014/064921 A1 | 5/2014 | |

OTHER PUBLICATIONS

Search Report regarding GB Application No. GB 1411615.6, dated Dec. 22, 2014, 4 pages.
Whatman Mini-UniPrep Syringeless Filter; "http://www.gelifesciences.com/webapp/wcs/stores/servlet/catalog/en/GELifeSciences-uk/products/AlternativeProductStructure_21502/28421655", accessed on Dec. 19, 2011, 1 page.
Chinese Office Action for CN Application No. 201580035640.9 dated Jun. 4, 2018 (13 pages, English translation).
European Office Action for EP Application No. 15729479.4 dated Nov. 9, 2018 (4 pages).

\* cited by examiner

DEVICE AND METHOD FOR CELL NUCLEI PREPARATION

CROSS-REFERENCE TO RELATED APPLICATIONS

This application is a filing under 35 U.S.C. 371 of international application number PCT/EP2015/063574, filed Jun. 17, 2015, which claims priority to GB application number 1411615.6, filed Jun. 30, 2014, the entire disclosures of each of which are hereby incorporated by reference.

TECHNICAL FIELD OF THE INVENTION

The present invention relates to the field of nucleic acid collection and storage, and in particular to the collection and long-term storage of nuclei. The invention provides a device and method which can be used to capture and store nuclei at ambient temperatures allowing the subsequent isolation of nucleic acids by passive washing with a wash buffer. The present invention finds application in the long term-storage and easy processing of nucleic acids and is particularly useful in genotyping, diagnostics and forensics.

DESCRIPTION OF RELATED ART

The challenge of shipping bloods from resource limited areas is well known and has encouraged the development of paper-based media to allow the drying and mailing of blood samples. This has been adopted broadly, including the World Health Organization, providing epidemiological surveys in HIV and other human pathogens and even those affecting birds, animals and plants. Long-term storage, transport and archiving of nucleic acids on filter paper or chemically-modified matrices is a well-known technique for preserving genetic material before the DNA or RNA is extracted and isolated in a form for use in genetic analysis such as the polymerase chain reaction (PCR).

EP1563091 (Smith et al, Whatman) relates to methods for storing nucleic acids from samples such as cells or cell lysates. The nucleic acid is isolated and stored for extended periods of time, at room temperature and humidity, on a wide variety of filters and other types of solid support or solid phase media. Moreover, the document describes methods for storing nucleic acid-containing samples on a wide range of solid support matrices in tubes, columns, or multiwell plates.

WO9003959 (Burgoyne) describes a cellulose-based solid support for the storage of DNA, including blood DNA, comprising a solid matrix having a compound or composition which protects against degradation of DNA incorporated into or absorbed on the matrix. This document also discloses methods for storage of DNA using the solid medium, and for recovery of or in situ use of DNA.

U.S. Pat. No. 5,705,345 (Lundin et al) describes a method of nucleic acid preparation whereby the sample containing cells is lysed to release nucleic acid and the sample is treated with cyclodextrin to neutralize the extractant. The advantage of this method is that it eliminates the need for a separation step which is required for the removal of the lysis reagent.

GB2346370 (Cambridge Molecular Technologies Ltd.) discloses a method involving applying a cellular sample containing nucleic acid to a filter, lysing the cells, then retaining the nucleic acid on the filter while removing contaminants.

WO9618731 (Deggerdal) describes a method of isolating nucleic acid whereby the sample is bound to a solid support and the sample is contacted with a detergent and subsequent steps performed to isolate the nucleic acid.

WO0053807 (Smith) discloses a medium for the storage and lysis of samples containing genetic material which can be eluted and analysed. The medium is coated with a lysis reagent and optionally with a weak base, a chelating agent, a surfactant or uric acid.

NUCLITIP (GE Healthcare; described in U.S. Pat. No. 5,447,864, Kenrick et al) is one of a number of known nuclei capture devices and consists of a microfilament weave of the tip of a pipette that processes up to 10 ml of fresh blood. The blood undergoes controlled lysis; the cell membrane is lysed leaving the majority of nuclei membrane intact. A planar treated membrane is located on the exterior of the Nuclitip pipette tip completely covering the tip's aperture such that the sample is filtered before entry into the tip and any DNA and nuclei present in the sample binds to the filter. The pipette tip is then washed with phosphate buffered saline (PBS) to remove any contaminants. U.S. Pat. No. 5,447,864 describes the method of separating cell components of cells using the NUCLITIP method and the possibility of storing the nuclei for longer periods on the membrane at −20° C. or below and for short periods if kept at 4° C. This document does not disclose or suggest the long term storage of cell nuclei at ambient temperatures. In addition the document suggests the use of standard nucleic acid extraction techniques including the use of detergents to lyse the nuclear membrane.

Ambient storage of biological samples is being seen as a better alternative to storage at low temperature. However, ambient storage has not widely replaced the use of cold chain shipping and freezer storage that is so typical of current biobanks. Application of GE Healthcare's FTA and 903 paper media is limited to the storage of a few 10's or 100's of microliters of blood which typically only provides up to 1 µg of DNA distributed over a large area of cellulose.

A number of international prospective studies are recruiting many thousands of participants in an effort to investigate links between the living environment, life-style and genetics with the onset of disease. For example the European Prospective Investigation into Cancer and Nutrition, and the Canadian Partnership for Tomorrow Project. The studies rely on in-depth analysis of the participants at the outset and subsequent analysis of DNA following diagnosis of a significant life-threatening disease sometime in the future. Moderate blood volumes of 4 ml or more are required when conducting large cohort studies to allow genetic analysis of samples using contemporary and evolving techniques. Ideally samples should contain material that would allow additional investigation of other important molecules, for example long non-coding RNA.

Such large prospective genetic screening studies demand much more DNA per patient than is possible using FTA and 903 paper media. Typically, prospective genetic screening studies require in the region of 10-200 µg genomic DNA. Many groups reluctantly maintain frozen VACUTAINER tubes.

Co-pending patent application number GB1313146.1 teaches a method for storing cell nuclei for extended periods at ambient temperature on a permeable membrane. The method involves selectively lysing the cytoplasmic membranes and a small proportion of the nuclear membranes present in a cellular sample to leave a large proportion of the cell nuclei intact, then collecting the cellular sample on the permeable membrane and then washing the permeable membrane and storing the intact nuclei on the permeable membrane at ambient temperature. The permeable membrane may also be submerged in an organic solvent such as ethanol or isopropanol prior to storage. The method is recited as being applicable for processing a cellular sample having a volume greater than 10 ml and for storage periods of up to 20 years. In the examples, 2 ml of human whole blood (collected in EDTA tubes) was added to lysis buffer and the nuclei captured using multiple NUCLITIPS, washed and stored for 60 days at ambient temperature, with the nucleic acid quality maintained over the storage period.

Although enabling for ambient temperature storage of greater amounts of nucleic acid, the exemplified methodology utilising multiple NUCLITIPS in patent application number GB1313146.1 is relatively cumbersome. There is therefore a need for improved means to store large volumes of cell nuclei at ambient temperatures for current and future analytical studies.

SUMMARY OF THE INVENTION

According to a first aspect of the present invention, there is provided a device (1) comprising:
(i) a container (2) having an open upper end (3) and sealed lower end (4) and a chamber (5) therebetween defined by chamber walls (6);
(iii) a plunger (7) comprising a hollow plunger body (8) defined by plunger walls (9) wherein said walls (9) have a shape corresponding to and a diameter less than said chamber (5), a septum cap (10) sealing a top end (11a) of said plunger body (8), and a solid support (12) spanning the diameter (d) of said plunger body (8).

In one embodiment of the device (1) of the invention said container (2) comprises a hollow tube (13) and a removable base (14).

In one embodiment, said chamber contains a lysis reagent. A particular lysis reagent for use in the context of the present invention is a red cell lysis buffer, a non-limiting example of which is a buffer containing a non-ionic surfactant, such as a sucrose-triton buffer, i.e. a buffer comprising sucrose and TRITON X-100 (ethoxylated octylphenol). Such a red cell lysis buffer is required where the device of the invention is used in the method of the invention described hereinbelow where the cellular sample introduced into the container is a whole blood sample. The lysis reagent may be water where the device of the invention is used in the method of the invention where the cellular sample is a saliva sample. In one embodiment, the lysis reagent is an anionic surfactant, non-limiting examples of which include sodium dodecyl sulfate (SDS), ammonium dodecyl sulfate, sodium laureth sulfate, sodium lauroyl sarcosinate, sodium myreth sulfate and sodium stearate.

In one embodiment of the device (1) of the invention, said chamber (5) further contains a collection buffer.

In one embodiment of the device (1) said solid support (12) is a permeable membrane, e.g. selected from the group consisting of polyester membrane, polyamide membrane, polycarbonate membrane and cellulose membrane. In a particular embodiment, said solid support is a polyester membrane.

In one embodiment of the device (1) of the invention said solid support (12) is located at a bottom end (11b) of said plunger body (8). In a particular embodiment of the device (1), said bottom end (11b) of said plunger body (8) seals the upper end (3) of said container (2) and wherein said chamber (5) comprises a vacuum.

According to a second aspect of the present invention, there is provided a method comprising:
(i) introducing a cellular sample (15) into a container (2) wherein said container (2) has an open upper end (3) and sealed lower end (4) and a chamber (5) therebetween defined by chamber walls (6) wherein said container (2) contains a collection buffer comprising a lysis reagent at a concentration sufficient to selectively lyse the cytoplasmic membranes and a small proportion of the nuclear membranes present in the cellular sample (15) and leave a large proportion of the cell nuclei intact;
(ii) inserting a plunger (7) into the upper end (3) of said container (2) wherein said plunger (7) comprises a hollow plunger body (8) defined by plunger walls, (9) wherein said walls (9) have a shape corresponding and a diameter less than said chamber (5), a septum cap (10) sealing the top end (11a) of said plunger body (8), and a solid support (12) spanning the diameter (d) of said plunger body (8);
(iii) pressing said plunger (7) towards said lower end (4) of said container (2) so that said solid support (12) passes through said cellular sample (15) and the cell nuclei and other cellular components bind to the solid support leaving filtrate behind; and,
(iv) removing said filtrate.

In various embodiments of the method of the invention said lysis reagent and said solid support are as defined hereinabove in relation to the various embodiments of the device of the invention.

In one embodiment of the method, said cellular sample (15) has a volume greater than 1 ml, particularly greater than 5 ml and more particularly greater than 10 ml.

In one embodiment of the method, said intact cell nuclei contain nucleic acid. Said nucleic acid in particular comprises deoxyribonucleic acid (DNA) or ribonucleic acid (RNA).

In one embodiment the method further comprises the step (v) of storing the intact nuclei on the solid support (12) at ambient temperature.

In one embodiment the method comprises the additional step of submerging the solid support (12) in an organic solvent after said washing step (iv) and before said storing step (v). The organic solvent may be an alcohol. Non-limiting examples of suitable alcohols include ethanol and isopropanol.

In one embodiment of the method, said solid support (12) is air dried prior to said storing step (v).

In one embodiment the method comprises the additional step (vi) of recovering the nucleic acid from the intact nuclei. In a particular embodiment said recovering step comprises lysing the intact nuclei on the solid support (12). In another embodiment, said recovering step comprises centrifugation following lysis of the intact nuclei, in particular using a microcentrifuge. In another embodiment, said recovering step is preceded by passive washing said solid support (12).

In one embodiment, said cellular sample (15) is introduced into said container (2) directly from a subject.

According to a third aspect of the present invention, there is provided a kit comprising the device of the invention and instructions for carrying out the method of the invention. All embodiments of the method and device of the invention described hereinabove are applicable to the kit of the invention.

DETAILED DESCRIPTION OF THE PREFERRED EMBODIMENTS

To more clearly and concisely describe and point out the subject matter of the claimed invention, definitions are provided in the description hereinbelow for specific terms used throughout the present specification and claims. Any exemplification of specific terms herein should be considered as non-limiting examples.

The term "Container" refers to any container suitable for collection of a cellular sample. Suitable containers are made of plastic and are substantially cylindrical. Non-limiting examples of suitable plastics for this purpose include polypropylene and polycarbonate. The chamber of the container has a volume in the range 2-10 ml, in one embodiment in the range 4-10 ml and in another embodiment 4-8 ml. In certain embodiments the container comprises a vacuum chamber. The container may comprise a hollow tube connected to a removable liquid-tight base.

In one embodiment, the device of the invention may be provided to the end user with a vacuum already present in the chamber, in a similar way to known VACUTAINER tubes for blood collection. In this embodiment the vacuum is created during the manufacturing process using methods well-known to those of skill in the art. Over time, the vacuum in such devices is released so in another embodiment, the device of the invention may be provided wherein the end user can create a vacuum in the chamber. In this latter embodiment, it is also possible to manufacture the device without creating a vacuum in the chamber so that the end user creates the vacuum, e.g. just before use of the device. One way for the end user to create a vacuum may be to start with the plunger in the lowered position and then close any ports on the device while pulling the plunger upwards. The vacuum once created would need to be maintained up to and including use of the device. Methods to maintain the vacuum include simply holding the plunger up. Alternatively it is envisaged that the device comprises a retaining mechanism to hold up the plunger once the vacuum has been created but that can be readily disturbed to allow the device to be used for collection of the cellular sample. Non-limiting examples of suitable retaining mechanisms include pins, collars and spring mechanisms of the type within the knowledge of those skilled in the art.

The term "Sealed" herein means liquid tight but not necessarily permanently sealed. In some embodiments the device is sealed sufficiently to maintain a vacuum in the chamber, e.g. with one or more sealing rings such as O-rings placed in the space between the chamber walls and the plunger.

The term "Plunger" refers to a component of the device of the invention that fits into the container and includes the solid support spanning at a lower end the entire internal diameter so that the solid support passes through the cellular sample in the container when the plunger is depressed. The walls of the plunger body are ideally of a diameter just a bit less than the diameter of the chamber of the container.

A "Septum Cap" can be understood to be any that incorporates a pierceable septum, e.g. made from silicone rubber. The septum cap is an integral part of the plunger and serves to maintain any vacuum within the device as well as permitting sample or filtrate to be removed where required. Furthermore, the septum cap permits use of the device for collection of cellular sample directly form a subject in a manner analogous to a VACUTAINER tube, i.e. with a butterfly needle having a needle at one end that punctures a subject's vein and a tube holder at the other end into which a device of the present invention comprising a vacuum in the chamber may be inserted in order to collect the cellular sample.

The term "Solid Support" as used herein includes but is not limited to cellulose-based products, cellulose, cellulose acetate, glass fibres, polyester, polyamide and polycarbonate or any combination thereof. A solid support of the present invention may be porous.

The term "Lysis Reagent" refers to any reagent that may be used for lysing the cellular membranes and selectively lysing the nuclear membranes of the cells in a cellular sample. The term "Lysing" is used herein to describe the process of rupturing, denaturing or puncturing a structure, such as a cellular or sub-cellular membrane, including a nuclear membrane.

The term "Collection Buffer" as used herein refers to any buffer suitable for collection of cellular samples for subsequent processing of nuclei and/or nucleic acids. Non-limiting examples of suitable collection buffers include citrate, heparin, acid citrate, dextrose and ethylenediaminetetraacetic acid (EDTA). In a particular embodiment the collection buffer is EDTA.

In one embodiment of the device of the invention, the chamber contains lysis buffer but does not contain collection buffer. This embodiment is particularly suited to use of the device of the invention to collect a cellular sample directly from a subject.

A "Subject" in the context of the present invention is any suitable eukaryotic organism which contains nuclei, such as human, animal, plant, avian, insect and fish.

In known methods for collecting cell nuclei onto a solid support, the cellular sample is collected in a separate step into a blood collection tube and then stored at refrigeration temperatures until processing. Often, such refrigerated samples are transported from the site of collection to the site of processing located elsewhere. In this context it is required to have a collection buffer present to avoid degradation of the sample, e.g. coagulation of a whole blood sample, which would prevent subsequent processing. In one embodiment of the method of the present invention, the sample is collected in situ directly from the subject and into the device. As such there is no requirement for a collection buffer to be present. The fresh cellular sample is immediately collected into lysis reagent so any degradation of the cellular sample, e.g. coagulation of a blood sample, does not have time to have any impact and therefore does not need to be inhibited by means of a collection buffer. A cellular sample can be collected into the chamber of the device at body temperature into the lysis buffer and a fair proportion of the blood cells would lyse straight away, in contrast to known methods where a low temperature sample would take longer to begin lysing. In this way a completely fresh cellular sample is collected and processed, in clear contrast to the known methods where cellular samples are separately collected. As well as being completely fresh, the cellular sample collected according to this embodiment does not comprise collection buffer, and consequently contains less chemical impurities meaning in turn that there are less impurities in the cellular sample that could interfere with its successful processing.

As used herein, the term "Cellular Sample" is used herein to refer to a fluid sample containing cellular material. The cellular material may originate from any suitable subject as defined hereinabove. The cellular material may for example be blood, saliva, urine, plasma.

"Nucleic Acid" as used herein refers to all forms of RNA (e.g. mRNA, lnRNA, miRNA, etc) and DNA (e.g. genomic DNA, mitochondrial DNA), as well as recombinant RNA and DNA molecules or analogues of DNA or RNA generating using nucleotide analogues, or mixtures thereof. The nucleic acid molecules can be single stranded or double stranded. In one embodiment, the term nucleic acid specifically refers to genomic nucleic acid.

The term "Other Cellular Components" in the present invention refers to the other solid cellular components besides the cell nuclei present in the cellular sample following lysis using the lysis reagent. These will include, amongst other known components, disrupted cell membranes, other organelles, haemoglobin from blood samples and proteins such as histone proteins.

The term "Filtrate" refers to the fluid left behind after the solid phase passes through the cellular sample in the method of the invention. This will be any component of the cellular sample that does not become bound to the solid phase after the solid phase is passed through the cellular sample in the method of the invention.

As used herein, the word "Storing" is used to describe the process of maintaining or preserving the nucleic acid in a stable condition.

The term "Organic Solvent" as used herein refers to any hydrocarbon-based solvent that is suitable for use in the storage of cell nuclei on a solid support.

As used herein, the term "Ambient Temperature" means a temperature in the range of 10° C. to 30° C., preferably 15° C. to 26° C., more preferably, 18° C. to 23° C.

The term "Air Dried" refers to the process of allowing solvent to evaporate from a solid support under ambient conditions without the application of additional heat or pressure.

The term "Recovering" refers to the step of removing nucleic acid from the solid support, generally following a period of storage. In this step, any cell nuclei bound to the solid support are lysed, e.g. by proteinase K digestion or other means known to those of skill in the art, and then removing the nuclei acid that has been released from the cell nuclei from the solid support, e.g. using centrifugation.

By the term "Passive Washing" is meant soaking the solid support in a wash buffer without taking any other active steps such as shaking. Passive washing can be carried out as part of recovering nucleic acid from the solid support and may be carried out either before or after storage. In one embodiment, passive washing is carried out after storage and after lysis of solid support-bound cell nuclei to release nucleic acid. The released nucleic acid is of a high molecular weight and is highly viscous therefore stays vigorously attached to the solid support. Passive washing therefore acts to release other cellular components from the solid support while leaving the released nucleic acid still bound. The wash buffer is removed after soaking by decanting or by pipetting, along with the other cellular components therein. The term "Wash Buffer" refers to any buffer solution suitable to remove other cellular components from the solid support. Non-limiting examples of a suitable wash buffers include phosphate-buffered saline (PBS) and $TE^{-1}$ ($TE^{-1}$ is a 10-fold diluted TE buffer known to those of skill in the art typically comprising 10 mM TRIS and 1 mM EDTA). One or more steps of passive washing may be carried out.

The term "Centrifugation" refers herein to the use of a centrifugal force to remove selected components from the solid support. When the solid support with cell nuclei is subjected to a short spin of centrifugation this serves to remove most of any fluid bound to the solid support and can be used as part of said removing step of the inventive method. Centrifugation can also be used as part of recovering nucleic acid from the solid support following storage, lysis of the cell nuclei and passive washing. Typically a microcentrifuge is sufficient to carry out centrifugation for the present invention.

The term "Kit" refers to a collection of components and reagents provided together in order to carry out the method of the present invention.

Figure 1:
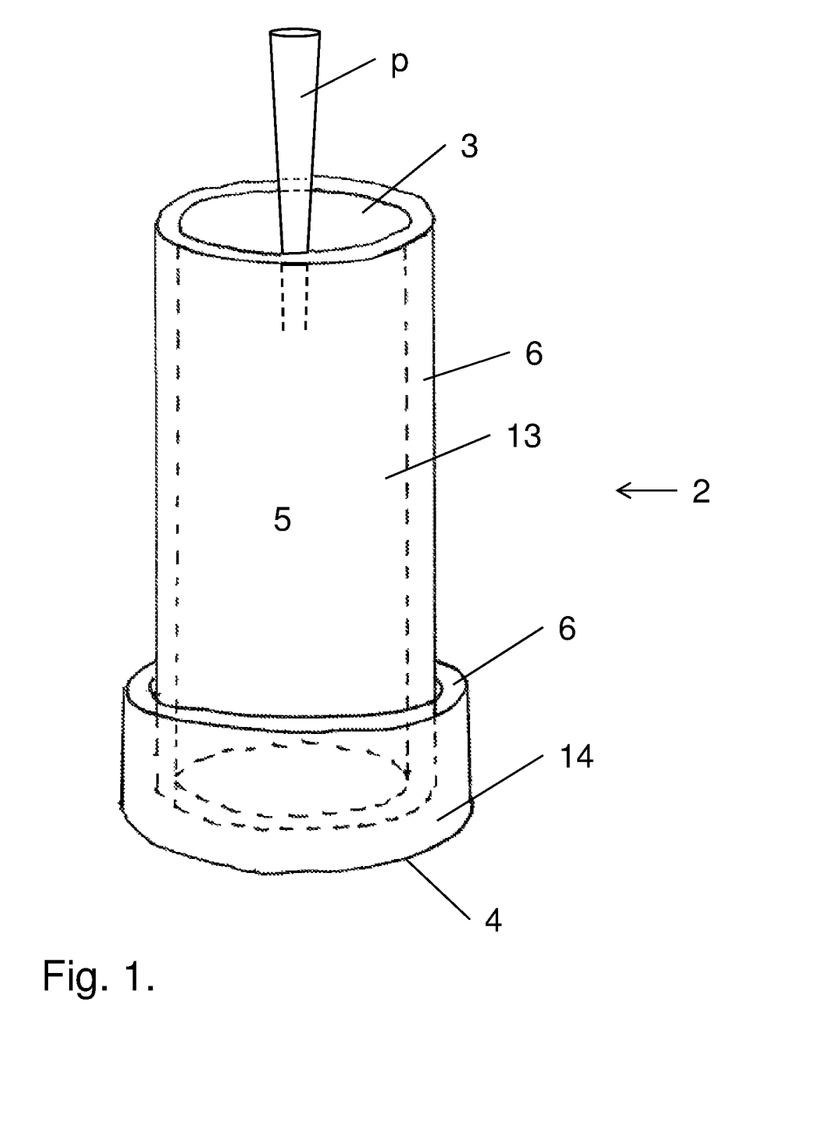
FIG. 1 illustrates how a sample can be added using a pipette (tip indicated by "p") to the chamber (5) of a container (2) of a device (1) of the invention.

FIG. 1 illustrates a container (2) suitable for the device (1) of the invention having an open upper end (3) and a sealed lower end (4) with a chamber (5) therebetween defined by chamber walls (6). The container shown comprises a hollow tube (13) and a removable base (14). The removable base (14) forms a liquid-tight seal around the hollow tube (13) in order to create a chamber (5) suitable for storage and processing of a cellular sample in the container (2). The cellular sample may collected separately in a blood collection tube, e.g. an EDTA tube, and the sample then added to the container (2) using a pipette (pipette tip "p" illustrated in FIG. 1).

Figure 2:
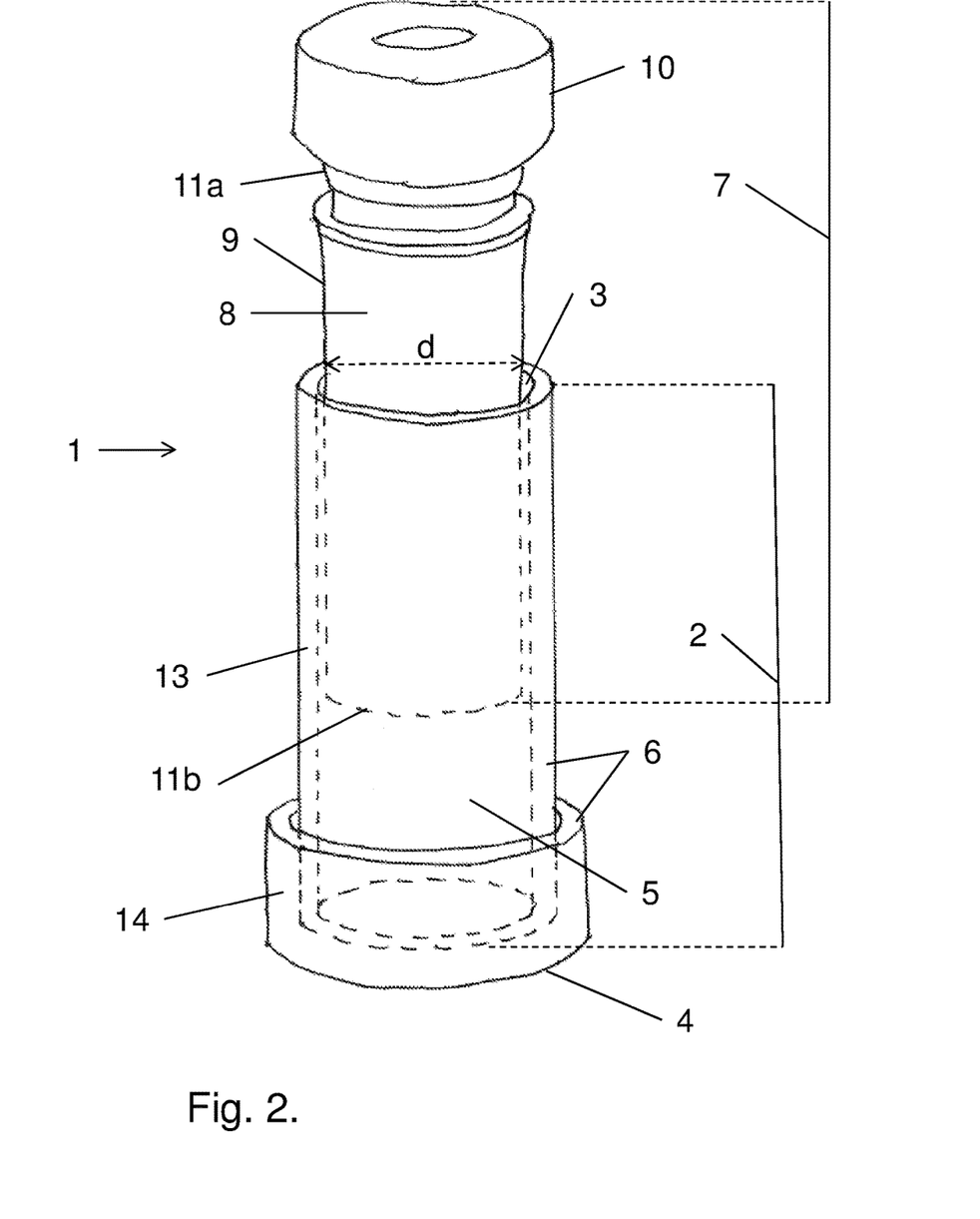
FIG. 2 illustrates a device (1) of the invention and the insertion of a plunger (7) into the container (2) of FIG. 1.

FIG. 2 shows the container (2) of FIG. 1 in association with a plunger (7) to form a device (1) of the invention. The components of the chamber (2) are as described above for FIG. 1. The plunger (7) is comprised of a hollow plunger body (8) defined by plunger walls (9) where these walls (9) are configured so that the plunger body (8) fits compatibly with the chamber (5) of the container (2) and can be pushed down into the chamber (5) without too much force being applied. The diameter (d) of the plunger body (8) should therefore be just less than the diameter of the chamber (5). At the top end (11a) the plunger (7) comprises a septum cap (10). At the bottom end (11b) of the plunger the solid support (not visible in FIG. 2) is positioned.

Figure 3:
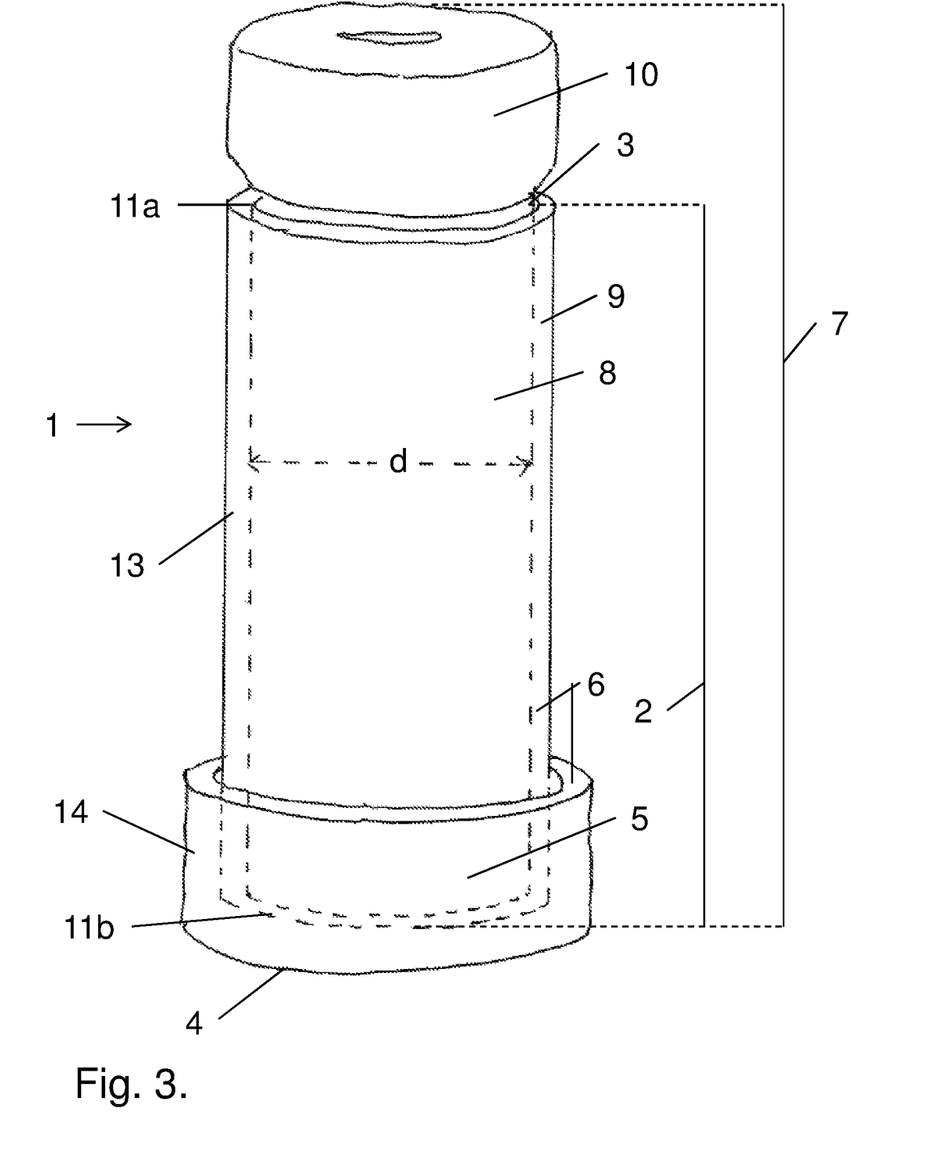
FIG. 3 shows the device (1) of FIG. 2 with the plunger (7) pushed down into the chamber (5) of the container (2).
Figure 4:
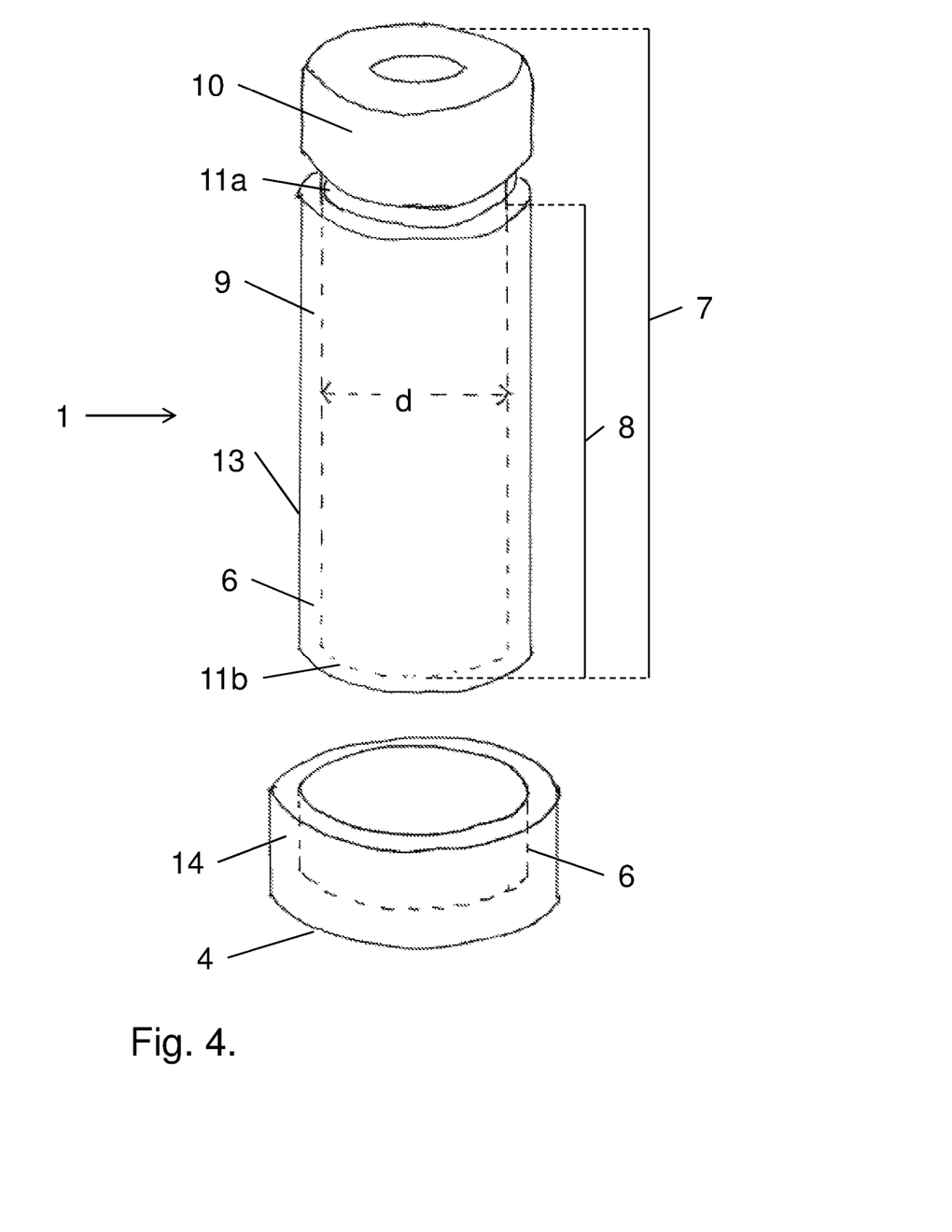
FIG. 4 shows the device (1) from FIGS. 2 and 3 wherein a removable base (14) of the container (2) has been removed, permitting access to the solid support (12) spanning the diameter (d) of the plunger body (8).

FIG. 3 shows the device (1) of FIG. 2 where the plunger (7) has been pushed into the chamber (5) of the container (2). The bottom end (11b) of the plunger body (8) is proximal to the lower end (4) of the container (2), in the position it would be in after passing the solid support (not visible in FIG. 3) through a cellular sample (not visible in FIG. 3) collected in said container (2). This position would also be that used for storage of the device (1). The base (14) can be removed to easily gain access to the nucleic acid and/or nuclei bound to the solid support. FIG. 4 shows the device (1) in this state with the base (14) removed.

Figure 5:
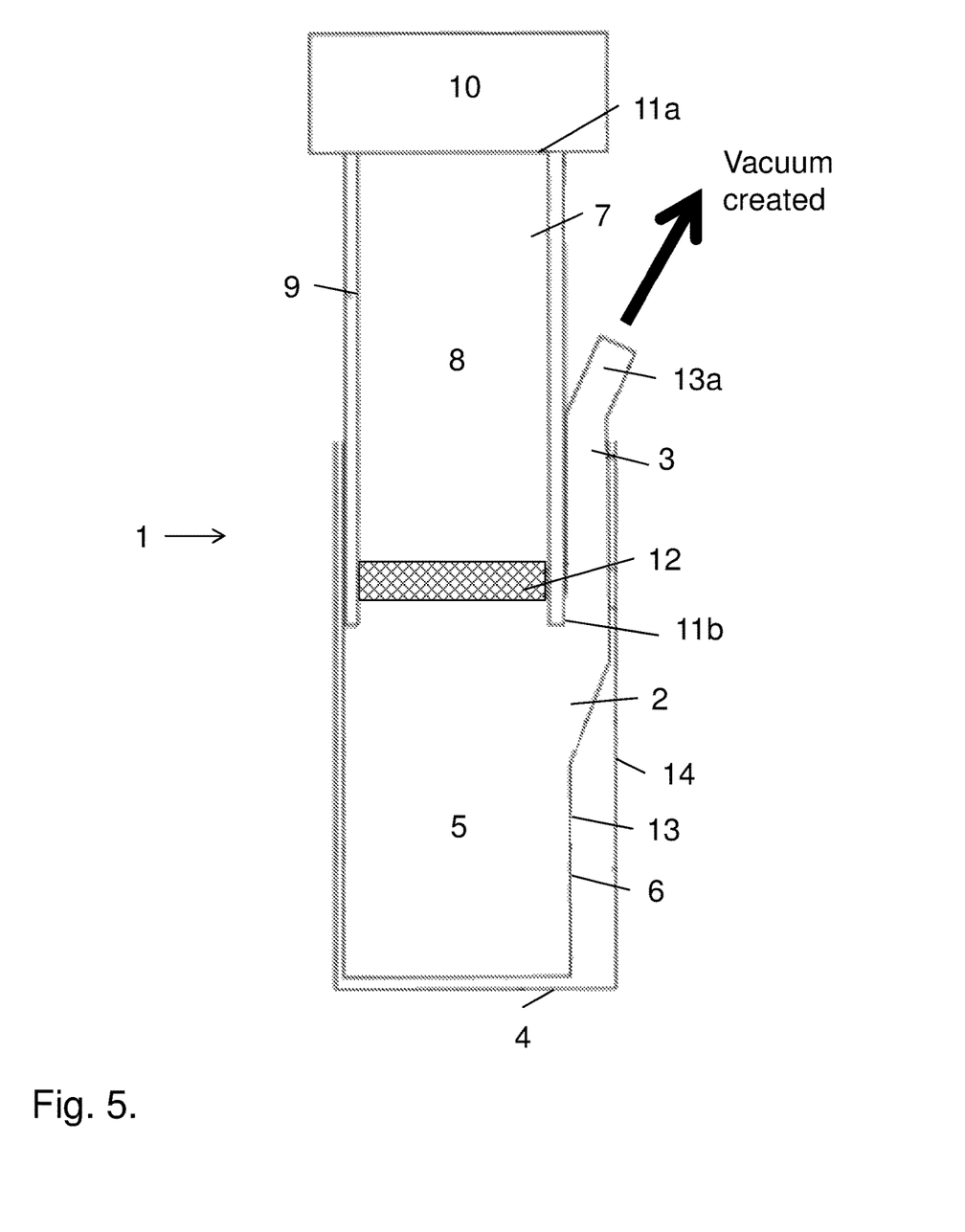
FIG. 5 illustrates a device (1) of the invention where the plunger (7) is inserted into the container (2) and a vacuum is being created (indicated by the arrow) within the chamber (5) of the container (2).

FIG. 5 shows the vacuum collection embodiment of the device (1) of the invention. The arrow illustrates the creation of a vacuum in the chamber (5) of the container (2). In the embodiment illustrated the container (2) comprises a hollow tube (13) and a base (14) where the hollow tube (13) includes a port (13a) connecting the chamber (5) to the exterior of the device (1). The port (13a) is used as illustrated in FIG. 5 for creation of a vacuum (shown with the arrow and also as illustrate in FIG. 6 for entry of the cellular sample (15) into the chamber (5). Alternatively when a side port is not used the standard device (1) shown in FIG. 2 can be used where pulling of the plunger (7) creates a negative pressure, when septum cap (10) and container (2) are sealed and then plunger (7) is raised.

Figure 6:
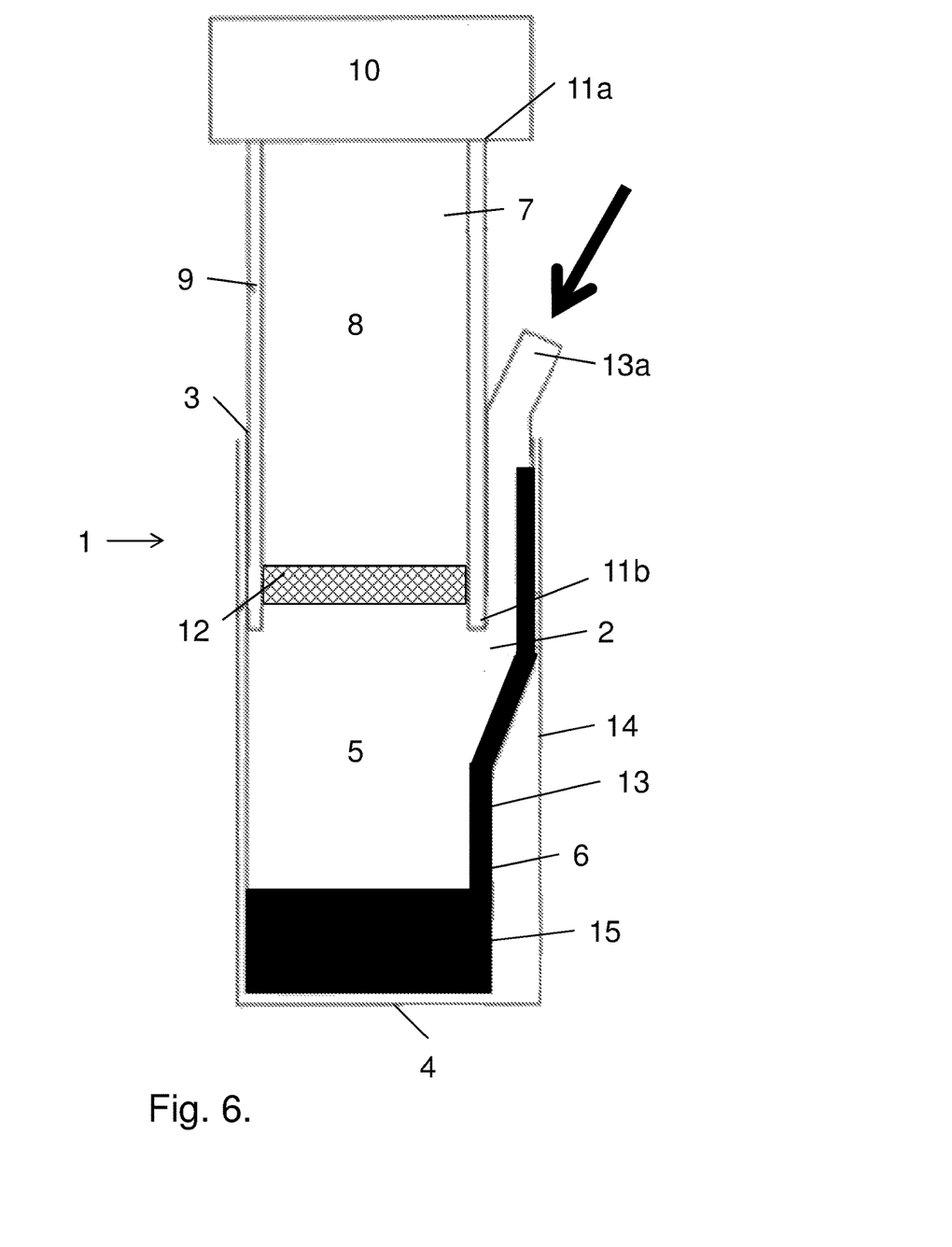
FIG. 6 illustrates use of the device (1) of FIG. 5 after the vacuum has been created in the chamber (5) of the container (2) to collect a cellular sample (15).
Figure 7:
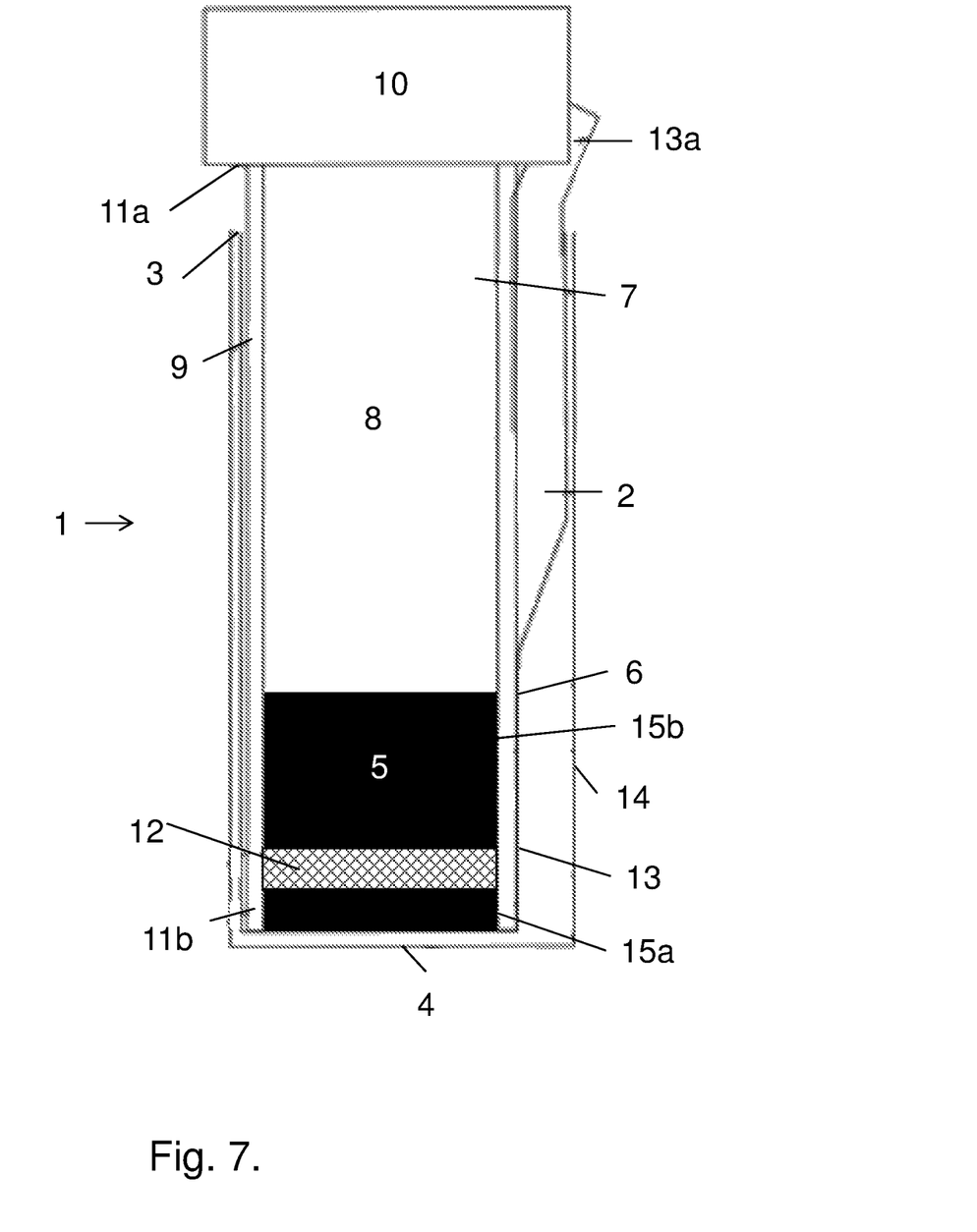
FIG. 7 illustrates the device of FIGS. 5 and 6 where the plunger (7) has been pushed down into the container (2) so that the solid support (12) has passed through some of the collected cellular sample (15b) and when pushed further will pass through the remaining cellular sample (15a).

FIG. 6 is the same device (1) as illustrated in FIG. 5 but after the vacuum has been created in the chamber (5) and in the process of collecting a cellular sample (15) into the chamber (5) via the port (13a). The plunger (7) is still in the raised position at this stage of the method of the invention. FIG. 7 shows the next stage of the method where the cellular sample (15) has been collected and the plunger (7) has been pressed down into the chamber (5) so that the solid support (12) is passing through the cellular sample (15).

The present invention exploits the known ability to harvest cell nuclei from multiple mls of blood to serve prospective genetic screening studies that typically require 10-200 µg genomic DNA. Compared to FTA paper an 80-fold increase is achieved with nuclei capture. This is owing to the fact that only nuclei are captured which are highly condensed packets of chromatin. It is likely that the reduced burden of heme and other contaminants will provide genomic DNA with a much better quality for downstream processing.

In one embodiment the device of the present invention is a Mini-UNIPREP-type device (GE Healthcare) designed to be able to be sealed sufficiently to withstand a negative pressure within and allows a blood sample to be withdrawn from a subject as is normal with VACUTAINER blood collection tubes (Becton Dickinson). This embodiment of the invention includes a special buffer to lyse red cells and allow capture of white cells or white cell nuclei on a membrane. Also, embodiments of the present invention include a removable top and base to allow access to captured nuclei.

In the method of the invention, after filling the device with blood and mixing end over end with the red cell lysis buffer, the plunger is moved up and down to capture cells on the membrane in a process that is reminiscent of using a NUCLITIP and a pipette to pump fluid back and forth across the membrane (described in detail in U.S. Pat. No. 5,447,864). Once this has been performed the device is opened and the cell- or nuclei-depleted blood is poured to waste and replaced by PBS and/or 100% ethanol (or alternative solvent) in a prescribed manner to wash and rapidly dry the trapped cells/nuclei.

Proof of principle experiments as set out in co-pending patent application number GB1313146.1 have shown that dried nuclei could be maintained at ambient temperature for more than 8 weeks without impacting the DNA quality, and it may be expected that the quality of DNA would be good for many years. In one embodiment of the invention a liquid-FTA buffer (a known buffer having a typical composition including SDS, uric acid, TRIS and EDTA) can be applied to the solid support after cell nuclei have been collected thereon, followed by drying, or dry organic solvent such as ethanol, or industrial methylated spirit or isopropyl alcohol or similar could be added to permanently maintain the tube at ambient temperature until samples are required, potentially many decades after collection. Storage of biological specimens in spirit is used throughout natural history museums and is a recognised method.

The preserved nuclei processed according to the method of the invention can be shipped at ambient and then placed in long term storage or a biobank.

When samples are to be processed, there are two modes:
1. Total preparation. Perform simple SDS proteinase k digestion and removal of contaminants to produce high yield of excellent quality genomic DNA for all downstream molecular biology applications. This is likely to require the device to be briefly centrifuged to recover the very viscous high molecular weight genomic DNA.
2. Sub-portion of single sample. Invert the tube (either dry or containing solvent), unscrew the base of the tube to reveal the outer apical surface of the membrane where nuclei/cells have been trapped, and using a spatula or abrading stick, twist or scrape to remove a sub-portion of the affixed cells or nuclei either manually or by an automated system. Said sample removed can be further processed or distributed to customers of the biobanks whilst the bulk stock can be returned to the store once end-cap has been replaced and tube has been inverted in storage location. It is suspected that up to 200 samples (assuming 100 µg and 0.5 µg per sampling) could be obtained from one device using this method.

The devices described and shown in the Figures could be interfaced with automation systems to provide unsupervised access to many hundreds of thousands of samples in an ambient storage repository. The device should have an outside diameter that is commensurate with ideal storage densities and required yields according to the demands of key opinion leaders. This approach is an alternative method in the way which genetic storage repositories could be utilised and maintained at minimal expense compared to the large sums of money required to run biobanks based on low temperature or liquid nitrogen. As an example of maintenance costs, contemporary biobanks can expect to pay millions of pounds each year to expand their operation, pay for electricity for low temperature storage and maintenance as well as ultra-low temperature dewars with nitrogen. This solution offers an opportunity to strip out some of the running costs of these facilities whilst maintaining the integrity of the sampled material stored. The limitations with the use of FTA are viably resolved with the present invention, which is a viable solution to a storage means for blood and biological samples.

The designs and descriptions provided herein allow in-field collection and pre-processing of bloods in resource limited regions and for shipping at ambient temperature and curation in biobanks.

The invention claimed is:
1. A device comprising:
(i) a container comprising an open upper end, a sealed lower end and a chamber therebetween defined by chamber walls; wherein said container further comprises a hollow tube adjacent the upper end allowing gaseous and liquid communication with the chamber and a removable base sealing the lower end, and wherein said chamber contains a cell lysis reagent;
(ii) a plunger comprising a hollow plunger body defined by plunger walls wherein said plunger walls have a shape conforming to and smaller than said chamber to allow a bottom end of the plunger to sealably slide within the chamber against the chamber walls, a septum cap sealing a top end of said plunger body, and a solid support spanning an interior transverse section of said plunger body, wherein said solid support is a permeable membrane; and

(iii) a vacuum port connected to the hollow tube, wherein negative pressure is created within the chamber through the hollow tube attached to the vacuum port.

2. The device as defined in claim 1, wherein said lysis reagent is a red cell lysis reagent.

3. The device as defined in claim 2, wherein said red cell lysis reagent is a sucrose-triton buffer.

4. The device as defined in claim 1, wherein said lysis reagent is water.

5. The device as defined in claim 1, wherein said lysis reagent is an anionic surfactant.

6. The device as defined in claim 5, wherein said chamber further contains a collection buffer.

7. The device as defined in claim 1, wherein said solid support is a permeable membrane selected from the group consisting of polyester membrane, polyamide membrane, polycarbonate membrane and cellulose membrane.

8. The device as defined in claim 7, wherein said solid support is a polyester membrane.

9. The device as defined in claim 8, wherein said solid support is located at the bottom end of said plunger body.

10. A method comprising:
(i) introducing a cellular sample into a container wherein said container has an open upper end and sealed lower end and a chamber therebetween defined by chamber walls, wherein said container further comprises a hollow tube adjacent the upper end allowing gaseous and liquid communication with the chamber, wherein negative pressure is created within the chamber through a vacuum port attached to the hollow tube, wherein said container contains a collection buffer comprising a lysis reagent at a concentration sufficient to selectively lyse the cytoplasmic membranes and a small proportion of the nuclear membranes present in the cellular sample and leave a large proportion of the cell nuclei intact;
(ii) inserting a plunger into the upper end of said container wherein said plunger comprises a hollow plunger body defined by plunger walls, wherein said walls have a shape conforming to and smaller than said chamber, a septum cap sealing the top end of said plunger body, and a solid support comprising a permeable membrane spanning an interior transverse section of said plunger body;
(iii) pressing said plunger towards said lower end of said container so that said solid support passes through said cellular sample and the cell nuclei and other cellular components bind to the solid support leaving filtrate behind; and,
(iv) removing said filtrate.

11. The method as defined in claim 10, wherein said lysis reagent is a red cell lysis reagent.

12. The method as defined in claim 11, wherein said red cell lysis reagent is a sucrose-triton buffer.

13. The method as defined in claim 10, wherein said lysis reagent is water.

14. The method as defined in claim 10, wherein said lysis reagent is an anionic surfactant.

15. The method as defined in claim 14, wherein said cellular sample has a volume greater than 1 ml.

16. The method as defined in claim 15, wherein said cellular sample has a volume greater than 5 ml.

17. The method as defined in claim 16, wherein said cellular sample has a volume greater than 10 ml.

18. The method as defined in claim 17, wherein said intact cell nuclei contain nucleic acid.

19. The method as defined in claim 18, wherein said nucleic acid comprises deoxyribonucleic acid (DNA) or ribonucleic acid (RNA).

20. The method as defined in claim 19, which further comprises the step (v) of storing the intact nuclei on the solid support at ambient temperature.

21. The method as defined in claim 20, comprising the additional step of submerging the solid support in an organic solvent after said removing step (iv) and before said storing step (v).

22. The method as defined in claim 21, wherein said organic solvent is an alcohol.

23. The method as defined in claim 22, wherein said alcohol is ethanol or isopropanol.

24. The method as defined in claim 23, wherein said solid support is air dried prior to said storing step (v).

25. The method as defined in claim 10, wherein said solid support is a permeable membrane selected from the group consisting of polyester membrane, polyamide membrane, polycarbonate membrane and cellulose membrane.

26. The method as defined in claim 25, wherein said solid support is a polyester membrane.

27. The method as defined in claim 26, which comprises the additional step (vi) of recovering a nucleic acid from the intact nuclei.

28. The method as defined in claim 27, wherein said recovering step (vi) comprises lysing the intact nuclei on the solid support.

29. The method as defined in claim 28, wherein said recovering step (vi) comprises centrifugation.

30. The method as defined in claim 29, wherein said recovering step is preceded by passive washing said solid support.

31. The method as defined in claim 30, wherein said cellular sample is introduced into said container directly from a subject.

32. A kit comprising the device as defined in claim 1 and instructions for carrying out the method of claim 10.

* * * * *